United States Patent [19]
Kaneko et al.

[11] Patent Number: 5,981,238
[45] Date of Patent: Nov. 9, 1999

[54] PROCESS FOR PRODUCING OPTICALLY ACTIVE AMINOPOLYCARBOXYLIC ACID

[75] Inventors: Makoto Kaneko; Yoshihiro Hashimoto; Takakazu Endo; Mami Kato; Wataru Mizunashi, all of Kanagawa, Japan

[73] Assignee: Mitsubishi Rayon Co., Ltd., Tokyo, Japan

[21] Appl. No.: 08/841,663

[22] Filed: Apr. 30, 1997

[30] Foreign Application Priority Data

| Apr. 30, 1996 | [JP] | Japan | 8-130594 |
| Aug. 20, 1996 | [JP] | Japan | 8-235797 |
| Jan. 31, 1997 | [JP] | Japan | 9-31399 |

[51] Int. Cl.⁶ ............................... C12P 13/20
[52] U.S. Cl. .................. 435/106; 435/109; 435/232; 562/565
[58] Field of Search ............ 562/565; 435/106, 435/109, 232

[56] References Cited

U.S. PATENT DOCUMENTS

| 3,158,635 | 11/1964 | Kezerian et al. |  |
| 3,198,712 | 8/1965 | Takahashi et al. |  |
| 4,880,738 | 11/1989 | Rozzell. |  |
| 5,466,867 | 11/1995 | Lin | 562/554 |
| 5,550,285 | 8/1996 | Layman | 562/565 |
| 5,554,791 | 9/1996 | Lin | 562/565 |
| 5,587,512 | 12/1996 | Lin | 562/565 |
| 5,707,836 | 1/1998 | Endo | 435/109 |

OTHER PUBLICATIONS

XP–002079982, *Chemical Abstracts,* vol. 69, No. 26, Dec. 23, 1968.

JP 60–168395A (Abstract), *Database WPI,* Section Ch, Week 8541, Aug. 31, 1995.

Nishikiori, Takaaki et al., "Production by Actinomycetes of (S,S,), N,N'–ethylendiaminedisuccinic acid, an inhibitor of phospholipase C", *J. Antibiot,* (1984).

*Primary Examiner*—Michael L. Shippen
*Attorney, Agent, or Firm*—Sughrue, Mion, Zinn, Macpeak & Seas, PLLC

[57] ABSTRACT

A process for producing an optically active aminopolycarboxylic acid, such as S,S-ethylenediamine-N,N'-disuccinic acid, from a mixture of a diamine, such as ethylenediamine, with fumaric acid using a microorganism having a lyase activity, wherein at least one metal ion selected from the group consisting of an alkaline earth metal, iron, zinc, copper, nickel, aluminum, titanium and manganese is added to the reaction system. According to this process, aminopolycarboxylic acids, such as S,S-ethylenediamine-N,N'-disuccinic acid, or metal complexes thereof, can be appropriately and efficiently produced while improving the reaction yield.

9 Claims, No Drawings

PROCESS FOR PRODUCING OPTICALLY ACTIVE AMINOPOLYCARBOXYLIC ACID

FIELD OF THE INVENTION

This invention relates to a process for producing an optically active aminopolycarboxylic acid from a diamine and fumaric acid using a microorganism. Optically active aminopolycarboxylic acids are capable of capturing heavy metal ions, and are highly biodegradable. Thus, they are useful as, for example, chelating agents and builders for detergents.

BACKGROUND OF THE INVENTION

Mixtures of optical isomers of aminopolycarboxylic acids represented by general formula (II) can be easily synthesized by organic synthetic techniques starting from various amines and maleic acid or fumaric acid. In the case of an optically active amino acid, however, optically active aspartic acid or the like must be used as the starting material in the organic synthesis. For example, it is reported that a mixture of the stereoisomers (S,S-, R,R- and meso-isomers) of a diaminoalkylene-N,N-disuccinic acid, which is a compound having two asymmetric carbon atoms in its molecule, can be chemically synthesized from maleic acid and various diamines (U.S. Pat. No. 3,158,635), while an optical isomer of this compound can be produced from L-aspartic acid and dibromoethane (John A. Neal et al., Inorganic Chem., 7, 2405 (1968)). However, L-aspartic acid and dibromoethane employed as the starting materials in the above process are relatively expensive, which makes it difficult to supply an inexpensive and commonly available optical isomer using said process.

With respect to microbial production, on the other hand, S,S-ethylenediamine-N,N'-disuccinic acid is isolated from the culture medium of Actinomycetes MG417-CF17A strain as a specific inhibitor of phospholipase C (T. Nishikiori et al., J. Antibiotics, 37, 426 (1984)). However, this microorganism only achieves an extremely low productivity. Thus, this production process is not industrially practical.

In contrast thereto, a novel process for efficiently producing an optically active diaminoalkylene-N,N'-disuccinic acid or the like from fumaric acid and various diamines using the catalytic action of a microorganism has been described (EP-A-0731171). An object of the present invention is to elevate the reaction yield in this process.

SUMMARY OF THE INVENTION

It has been found in the present invention that the reaction yield of the aminopolycarboxylic acid can be remarkably elevated by adding to the reaction system a metal ion with which the aminopolycarboxylic acid coordinates, to thereby form a complex.

Accordingly, the present invention provides a process for producing an optically active aminopolycarboxylic acid represented by the following general formula (II) comprising reacting a mixture of a diamine represented by the following general formula (I) with fumaric acid using a microorganism having a lyase activity or an extract thereof, wherein said reacting is carried out in the presence of at least one metal ion selected from the group consisting of an alkaline earth metal, iron, zinc, copper, nickel, aluminum, titanium and manganese:

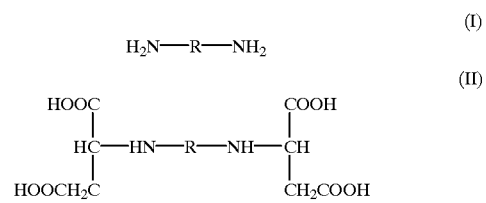

wherein R represents an alkylene, cyclohexylene or phenylene group.

DETAILED DESCRIPTION OF THE INVENTION

The reaction mechanism of the present invention, the gist of which is as described above, is assumed to be as follows. First, an optically active aminopolycarboxylic acid is formed from fumaric acid and a diamine using a microorganism having a lyase activity, which has been optionally processed. Subsequently, the aminopolycarboxylic acid thus formed coordinates with the metal ion contained in the reaction system more strongly than with fumaric acid or the diamine employed as the substrate, to thereby form a highly stable complex. Thus, the chemical equilibrium point shifts toward the product side. In other words, the equilibrium reaction of the formation of the stable complex joins in the equilibrium reaction of the formation of the optically active aminopolycarboxylic acid from fumaric acid and the diamine. It is assumed that, as a result, the total yield of the aminopolycarboxylic acid (namely, the sum of the free aminopolycarboxylic acid and its metal complex) is increased compared with the case where no metal is added.

The metal ions usable in the present invention are ions of alkaline earth metals, iron, zinc, copper, nickel, aluminum, titanium and manganese, such as Mg(II), Ca(II), Sr(II), Ba(II), Fe(II), Fe(III), Zn(II), Cu(II), Ni(II), Al(III), Ti(IV) and Mn(II) ions and various complex ions thereof.

As the sources of these metal ions, use can be made of hydroxides and oxides of these metals, salts of these metals with inorganic or organic acids, such as sulfuric, hydrochloric, nitric, phosphoric, carbonic and acetic acids, minerals containing these metal compounds and compounds of these metals with fumaric acid or diamines to be used as the substrate in the present invention. It is also possible to use a mixture of two or more of these compounds.

Generally, some kinds of metal hydroxide and metal oxide, such as ferric hydroxide and ferric oxide, are poorly or hardly soluble in water. However, it is also possible to use such a compound at a concentration exceeding the saturation level, for example, in a suspended state, since the metal compound can be solubilized in a considerable amount owing to the ability of the optically active aminopolycarboxylic acid to coordinate. That is to say, any compound may be used as the "metal ion" source in the present invention, so long as the metal ion coordinates with the aminopolycarboxylic acid so as to achieve the effect of the present invention.

Thus, it doesn't matter whether all or a part of the metal in metal compounds is present in the form of ion.

As described above, the present invention is based on the phenomenon that the metal ion causes a shift of the chemical equilibrium point from the substrate side to the product side. In general, the chemical equilibrium point is not affected by catalysts. In the present invention, accordingly, the chemical equilibrium point varies depending exclusively on the type of the metal ion and remains constant regardless of catalysts, unless being affected by side reactions or other reactions. That is to say, the microbial origin of the lyase serving as the catalyst in the present invention is not particularly restricted, so long as it is capable of forming the optically active aminopolycarboxylic acid.

Examples of the compound having an amino group represented by general formula (I) include alkylenediamines, such as ethylenediamine, 1,2-propanediamine, 1,3-propanediamine and 2-methyl-1,3-propanediamine, cyclohexylenediamines, such as 1,2-, 1,3- and 1,4-cyclohexylenediamines and phenylenediamines, such as 1,2-, 1,3- and 1,4-phenylenediamines.

Typical examples of the optically active aminopolycarboxylic acid represented by general formula (II) obtained by the present invention include alkylenediamine, cyclohexylenediamine and phenylenediamine-N,N'-disuccinic acids corresponding to the above-mentioned diamines such as S,S-ethylenediamine-N,N'-disuccinic acid, 1,2-propanediamine-N,N'-disuccinic acid, 1,3-propanediamine-N,N'-disuccinic acid, 2-methyl-1,3-propanediamine-N,N'-disuccinic acid, 1,2-cyclohexylenediamine-N,N'-disuccinic acid, 1,3-cyclohexylenediamine-N,N'-disuccinic acid, 1,4-cyclohexylene-diamine-N,N'-disuccinic acid, 1,2-phenylenediamine-N,N'-disuccinic acid, 1,3-phenylenediamine-N,N'-disuccinic acid and 1,4-phenylene-N,N'-diaminedisuccinic acid.

In a particularly preferable embodiment of the present invention, the diamine of the general formula (I) is ethylenediamine, and the optically active aminopolycarboxylic acid of the general formula (II) is S,S-ethylenediamine-N,N'-disuccinic acid.

Examples of the microorganism having a lyase activity include bacteria belonging to the genera Hafnia, Burkholderia, Acidovorax, Pseudomonas, Arthrobacter, Paracoccus, Sphingomonas and Brevundimonas.

More particularly, examples of such strains include: *Hafnia alvei* ATCC 9760 strain, *Burkholderia sp.* KK-5 strain (FERM BP-5412), ibid. KK-9 strain (FERM BP-5413), *Acidovorax sp.* TN-51 strain (FERM BP-5416), *Pseudomonas sp.* TN-131 strain (FERM BP-5418), *Arthrobacter sp.* KK-3 strain (FERM BP-5414), *Paracoccus sp.* KK-6 strain (FERM BP-5415), *Sphingomonas sp.* TN-28 strain (FERM BP-5419), *Brevundimonas sp.* TN-30 strain (FERM BP-5417) and ibid. TN-3 strain (FERM BP-5886).

Among these bacteria, the ATCC 9760 strain is a publicly known one and can be easily obtained from the American Type Culture Collection (ATCC).

Other bacteria have been newly isolated from nature and deposited at National Institute of Bioscience and Human-Technology, Agency of Industrial Science and Technology under the accession numbers as defined above. The mycological properties thereof are as follows.

| Bacteriological property | KK-5 strain | KK-9 strain |
|---|---|---|
| morphology | bacillus | bacillus |
| gram staining | − | − |
| spore | − | − |
| motility | + | + |
| flagellum | polar | polar |
| attitude to oxygen | multitrichous aerobic | multitrichous aerobic |
| oxidase | + | + |
| catalase | + | + |
| OF test | O | O |
| quinone type | Q-8 | Q-8 |
| cleavage of protocatechuate | ortho-type | ortho-type |
| formation of fluorochrome | − | − |
| reduction of nitrate | − | + |
| formation of indole | − | − |
| arginine dihydrolase | − | − |
| decomposition of urea | − | − |
| decomposition of esculin | − | − |
| liquefaction of gelatin | − | − |
| PNPG | + | − |
| formation of acid from xylose | + | + |
| utilization for growth: | | |
| glucose | + | + |
| L-arabinose | + | + |
| D-mannose | + | + |
| D-mannitol | + | + |
| maltose | − | − |
| potassium gluconate | + | + |
| n-capric acid | + | + |
| adipic acid | − | − |
| dl-malic acid | + | + |
| citric acid | + | − |
| phenyl acetate | + | + |

| TN-51 strain | |
|---|---|
| morphology | bacillus |
| gram staining | − |
| spore | − |
| motility | + |
| flagellum | polar |
| attitude to oxygen | aerobic |
| oxidase | + |
| catalase | + |
| OF test | O |
| colony color | forming no characteristic pigment |
| accumulation of PHB | + |
| growth at 40° C. | − |
| cleavage of protocatechuate | meta-type |
| carotenoid pigment | − |
| utilization of glucose for growth | + |
| ability to utilize hydrogen | − |
| quinone type | Q-8 |

| TN-131 strain | |
|---|---|
| morphology | bacillus |
| gram staining | − |
| spore | − |
| motility | + |
| flagellum | polar |
| attitude to oxygen | aerobic |
| oxidase | + |
| catalase | + |
| OF test | − |
| colony color | yellowish |
| formation of fluorochrome | + |
| quinone type | Q-9 |
| reduction of nitrate | + |
| formation of indole | − |
| arginine dihydrolase | − |
| decomposition of urea | − |
| decomposition of esculin | − |
| liquefaction of gelatin | − |

| Bacteriological property | |
| --- | --- |
| PNPG | + |
| utilization for growth: | |
| glucose | − |
| L-arabinose | − |
| D-mannose | − |
| D-mannitol | − |
| N-acetyl-D-glucosamine | − |
| maltose | − |
| potassium gluconate | − |
| n-capric acid | + |
| adipic acid | − |
| dl-malic acid | + |
| citric acid | + |
| phenyl acetate | − |
| | KK-3 strain |
| morphology | polymorphic bacillus |
| gram staining | + |
| spore | − |
| motility | − |
| attitude to oxygen | aerobic |
| oxidase | − |
| catalase | + |
| colony color | forming no characteristic pigment |
| acid-fastness | − |
| rod-coccus cycle | + |
| elongation around colony | none |
| diamino acid in cell wall | lysine |
| glycolyl test | − (acetyl type) |
| arabino-galactan polymer in cell wall | − (assumed by acid-hydrolysis product of whole cells) |
| quinone type | MK-9 (H$_2$), 8 (H$_2$) |
| GC content of DNA | 65 mol (%) (determined by HPLC) |
| | KK-6 strain |
| morphology | spherical - short bacillus |
| gram staining | − |
| spore | − |
| motility | − |
| flagellum | − |
| attitude to oxygen | aerobic |
| oxidase | + |
| catalase | + |
| OF test | − |
| colony color | forming no characteristic pigment |
| formation of fluorochrome | − |
| accumulation of PHB | + |
| reduction of nitrate | + |
| quinone type | Q-10 |
| GC content of DNA | 64 mol % (determined by HPLC). |
| | TN-28 strain |
| morphology | bacillus |
| gram staining | − |
| spore | − |
| motility | + |
| flagellum | polar |
| attitude to oxygen | aerobic |
| oxidase | + |
| catalase | + |
| OF test | − |
| colony color | yellowish |
| formation of fluorochrome | − |
| quinone type | Q-10 |
| reduction of nitrate | − |
| formation of indole | − |
| arginine dihydrolase | − |
| decomposition of urea | − |
| decomposition of esculin | + |
| liquefaction of gelatin | − |
| PNPG | − |
| utilization for growth: | | |
| glucose | + | |
| L-arabinose | − | |
| D-mannose | + | |
| D-mannitol | − | |
| N-acetyl-D-glucosamine | + | |
| maltose | + | |
| potassium gluconate | − | |
| n-capric acid | − | |
| adipic acid | − | |
| dl-malic acid | + | |
| citric acid | − | |
| phenyl acetate | − | |
| | TN-30 strain | TN-3 strain |
| morphology | bacillus | bacillus |
| gram staining | − | − |
| spore | − | − |
| motility | + | + |
| flagellum | polar | polar |
| attitude to oxygen | aerobic | aerobic |
| oxidase | + | + |
| catalase | + | + |
| OF test | − | − |
| colony color | forming no characteristic pigment | |
| formation of fluorochrome | − | − |
| accumulation of PHB | + | + |
| auxotrophy | + | + |
| quinone type | Q-10 | Q-10 |
| reduction of nitrate | + | + |
| formation of indole | − | − |
| arginine dihydrolase | − | − |
| decomposition of urea | − | − |
| decomposition of esculin | − | − |
| liquefaction of gelatin | − | − |
| PNPG | − | − |
| utilization for growth: | | |
| glucose | − | − |
| L-arabinose | − | − |
| D-mannose | − | − |
| D-mannitol | − | − |
| N-acetyl-D-glucosamine | − | − |
| maltose | − | − |
| potassium gluconate | + | + |
| n-capric acid | − | − |
| adipic acid | + | |
| dl-malic acid | − | + |
| citric acid | + | + |
| phenyl acetate | − | − |

Based on the above-mentioned bacteriological properties, these strains were identified in accordance with Bergey's Manual of Systematic Bacteriology Vol. 1 (1984) and Bergey's Manual of Determinative Bacteriology, 9th ed. (1994). As a result, it has been determined that the KK-5 and KK-9 strains belongs to the genus Burkholderia, the TN-51 strain belongs to the genus Acidovorax and the TN-131 strain belongs to the genus Pseudomonas. Further, it has been determined that the KK-3 strain belongs to the genus Arthrobacter in accordance with Bergey's Manual of Systematic Bacteriology Vol. 2 (1986); the KK-6 strain belongs to the genus Paracoccus in accordance with Bergey's Manual of Systematic Bacteriology Vol. 1 (1984); the TN-28 strain belongs to the genus Sphingomonas in accordance with Bergey's Manual of Determinative Bacteriology 9th ed. (1994) and Microbiol. Immnunol. 34, 99 (1990); and the TN-30 and TN-3 strains belong to the genus Brevundimonas in accordance with Bergey's Manual of Determinative Bacteriology 9th ed. (1994) and Int. J. Syst. Bacteriol. 44, 499 (1994).

Fumarase, which widely occurs in nature, hydrates fumaric acid serving as the substrate in the reaction of the present invention, and thus causes a decrease in the yield. Therefore, it is desirable that to eliminate or inhibit fumarase contained in the strain employed, unless the fumarase in the strain has a weak activity or can be easily inactivated. Examples of the methods known for inactivating fumarase include one wherein fumarase is eliminated from a disrupted cell suspension by chromatography, salting out, electrophoresis or the like, one wherein fumarase is inhibited with an inhibitor and one wherein fumarase is inactivated while maintaining the cells (I. Umehara et al., Appl. Microbial. Biotechnol., 20, 291 (1984); and Yukawa et al., Nogei Kagaku (Agricultural Chemistry), 59, 279 (1985)).

Next, a general mode for carrying out the present invention will be described.

The medium to be used for incubating the microorganism in the present invention is not particularly restricted. Namely, either a synthetic medium or a natural one may be used so long as it contains appropriate carbon sources, nitrogen sources and inorganic salts which can be metabolized by the microorganism together with trace amounts of organic nutrients, etc. In the incubation, it is preferable to add ethylenediamine-N,N'-disuccinic acid, ethylenediamine-N-monosuccinic acid, amino acids such as aspartic acid, glutamic acid and histidine and fumaric acid to the medium, since cells with the elevated desired activity can be sometimes obtained thereby. The incubation conditions vary depending on the cells and medium. In general, the pH value of the medium ranges from 4 to 10, preferably from 6 to 9, and the incubation temperature ranges from 20 to 45° C., preferably from 25 to 35° C. The incubation may be performed under aerobic conditions for 1 to 10 days until the activity attains the maximum level.

In general, the reaction for producing an optically active aminopolycarboxylic acid in the present invention is carried out by reacting a mixture of the diamine and fumaric acid in an aqueous solution (including adding the same to culture medium) containing the metal ion, in the presence of the microorganism, or extract thereof having lyase activity ("processed microorganism"). As used herein, the term "microorganism" includes dry cells, as well as immobilized cells. Further, as used herein, the term "extract includes disrupted cells, crude or purified lyase activity obtained thereform and immobilized lyase activity obtained therefrom.

Fumarase free active fractions are prepared from the cells having a lyase activity. The cells are disrupted and centrifuged to remove insoluble outer membrane fractions. The active fraction is separated from fumarase activity as a precipitates by ammonium sulfate followed by DEAE-Sephacel column chromatography.

The concentrations of the diamine ranges from 0.01M to 2M, preferably from 0.015M to 1M, and that of fumaric acid ranges from 0.01M to the saturation, preferably from 0.02M to 0.6M, though they may vary depending on the reaction temperature and pH value. The metal compound is employed usually in an amount 0.01 to 2 times by mol, preferably 0.2 to 1.5 times by mol, in terms of the metal, as much as the theoretical amount of the optically active aminopolycarboxylic acid product. The metal compound may be added either at once at the initiation of the reaction or in the course of the reaction.

The optionally processed microorganism is used usually in an amount of 0.01 to 5% by weight, in terms of dry cells, based on the substrate.

The pH value of the reaction mixture ranges from 4 to 11, preferably from 6 to 10.

The reaction is carried out usually at 5 to 60° C., preferably at 10 to 55° C. From the viewpoint of reaction rate, a higher temperature is the more advantageous. However, the reaction of the formation of the optically active aminopolycarboxylic acid from the diamine and fumaric acid and the reaction for forming the metal complex are both exothermic ones. Therefore, a lower temperature is the more advantageous from the viewpoint of reaction yield. Accordingly, it is possible to perform the reaction at a high temperature in the early stage, and then lower the reaction temperature.

The reaction may be performed either batchwise or continuously.

It is also possible that a reaction system for synthesizing the diamine and fumaric acid from any materials coexists with the reaction system of the present invention, so long as the effects of the present invention can be thus achieved.

When it is needed to obtain a metal complex of the optically active aminopolycarboxylic acid, the reaction is performed in the presence of a definite metal ion followed by pH regulation, concentration and the like so as to directly obtain the desired compound.

To recover the optically active aminopolycarboxylic acid from the mixture after the completion of the reaction, on the other hand, it is a practice to effect precipitation with the use of a mineral acid. In the case of such a reaction system wherein a stable complex is formed at the pH value of the acid precipitation as the one where the reaction is carried out in the presence of a heavy metal ion, such as iron ion, it is necessary to eliminate the metal ion prior to the acid precipitation. When an optically active aminopolycarboxylic acid is needed, therefore, it is efficient to carry out the reaction in the presence of an alkaline earth metal ion, such as calcium ion, thus omitting the above-mentioned procedure for the elimination.

To further illustrate the present invention in greater detail, the following non-limiting Example is provided.

EXAMPLE 1

(1) Cultivation:

The strains *Hafinia alvei* ATCC 9760, *Burkholderia sp.* KK-5 and KK-9, *Acidovorax sp.* TN-51, *Pseudomonas sp.* TN-131, *Arthrobacter sp.* KK-3, *Paracoccus sp.* KK-6, *Sphingomonas sp.*

TN-28 and *Brevundimonas sp.* TN-30 and TN-3 were each taken up one platinum loopful, from a slant culture and inoculated into the medium specified below, and the strain was cultivated aerobically under shaking at 30° C. for 3 days.

Medium composition (pH 7.5, 100 ml):

| | |
|---|---|
| ethylenediamine-N,N'-disuccinic acid | 0.2 g |
| glucose | 0.2 g |
| yeast extract | 0.1 g |
| polypeptone | 0.05 g |
| magnesium sulfate.7H$_2$O | 0.1 g |
| sodium sulfate | 0.28 g |
| phosphate buffer | 25 mM |
| solution of metal salt mixture* | 0.5 ml |

* Solution of metal salt mixture (100 ml): magnesium chloride.6H$_2$O 0.8 g, calcium chloride 0.8 g, manganese sulfate.4H$_2$O 0.6 g, ferric chloride.6H$_2$O 0.12 g, and zinc sulfate 0.06 g.

(2) Acquisition of Cell:

20 ml of the culture medium was introduced into a centrifugal tube and centrifuged at 10,000 rpm at 5° C. for 15 minutes. The cells thus harvested were washed with a 50 mM phosphate buffer (pH 8.0) twice.
(3) Reaction:

As the reaction mixture, use was made of one containing 200 mM of fumaric acid, 200 mM of ethylenediamine, 100 mM of magnesium salt and the above-mentioned cells, having been adjusted to pH 8.0 with 6 N sodium hydroxide. For comparison, a mixture of the same composition but being free from magnesium sulfate was employed. These mixtures were each reacted at 30° C. under shaking for 24 hours.

After the completion of the reaction, the S,S-ethylenediamine-N,N'-disuccinic acid (S,S-EDDS) thus produced was determined, e.g., by removing any suspended solids via centrifugation at 15,000 rpm at 5° C. for 5 minutes, and/or subjecting the resulting supernatant (reaction mixture) to liquid chromatography using WAKO-SIL 5C8 (manufactured by Wako Pure Chemical Industries, Ltd.; eluent: 50 mM phosphate buffer (pH 2) containing 10 mM of tetra-n-butylammonium hydroxide and 0.4 mM of $CuSO_4$) and MCI GEL CRS 10W (manufactured by Mitsubishi Chemical Industries, Ltd., eluent: 10 mM $CuSO_4$).

The product was isolated and purified by the method using an ion exchange resin reported by T. Nishikiori et al., J. Antibiotics 37, 426 (1984). After obtaining crystals, the chemical structure of the product was confirmed by NMR and mass spectrometry.
(4) Results:

TABLE 1

| Strain | Magnesium salt (100 mM) | S,S-EDDS formed (mM) |
|---|---|---|
| TN-3 | none | 14.0 |
|  | magnesium sulfate | 31.2 |
|  | magnesium chloride | 29.6 |
| ATCC 9760 | none | 0.3 |
|  | magnesium chloride | 0.5 |
| KK-5 | none | 8.4 |
|  | magnesium chloride | 28.5 |
| KK-9 | none | 5.4 |
|  | magnesium chloride | 23.4 |
| TN-51 | none | 11.6 |
|  | magnesium chloride | 30.1 |
| TN-131 | none | 17.6 |
|  | magnesium chloride | 22.4 |
| KK-3 | none | 0.1 |
|  | magnesium chloride | 0.2 |
| KK-6 | none | 9.2 |
|  | magnesium chloride | 19.6 |
| TN-28 | none | 10.1 |
|  | magnesium chloride | 25.5 |
| TN-30 | none | 19.0 |
|  | magnesium chloride | 35.5 |

EXAMPLE 2

(1) Cultivation:

The strains *Brevundimonas sp.* TN-3, *Sphingomnonas sp.* TN-28 and *Pseudomonas sp.* TN-131 were each taken up one platinum loopful, from a slant culture and inoculated into the medium described in Example 1, and the strain was cultivated aerobically under shaking at 30° C. for 4 days.
(2) Acquisition of Active Fraction Free from Fumarase, etc.:

20 ml of the culture medium was introduced into a centrifugal tube and centrifuged at 10,000 rpm at 5° C. for 15 minutes. The cells thus harvested were washed with a 50 mM phosphate buffer (pH 8.0) twice. Next, these cells were ultrasonicated at 50 W for 5 minutes and centrifuged at 10,000 rpm for 20 minutes to thereby give a crude enzyme solution. After precipitation with 60%-saturated ammonium sulfate and desalting by dialysis, the resulting extract was adsorbed by DEAE-Sephacel (manufactured by Pharmacia) equilibrated with a 50 mM phosphate buffer (pH 8.0) and developed therefrom with a linear gradient from the above-mentioned buffer to the same one containing 0.6 M of sodium chloride. If needed, the above procedure was repeated but using HPLC (TSK-gel DEAE-5PW manufactured by Tosoh) as a substitute for the DEAE-Sephacel to thereby give a fraction from which matters capable of reducing fumaric acid such as fumarase had been eliminated as far as possible.
(3) Reaction:

As the reaction mixture, use was made of one containing 68.4 mM of fumaric acid, 34.2 mM of ethylenediamine, 200 mM of a borate buffer, 17.1 mM of magnesium sulfate and the above-mentioned active fraction, having been adjusted to pH 8.0 with 6 N sodium hydroxide. For comparison, a mixture of the same composition but being free from magnesium sulfate was employed. These mixtures were each reacted at 30° C. for 4 to 10 days until S,S-EDDS was scarcely formed any more. During this process, the pH value of each reaction mixture was maintained at 8 with 6 N sodium hydroxide.

After the completion of the reaction, S,S-EDDS in the mixture was determined by the same method as the one employed in Example 1.
(4) Results:

TABLE 2

| | S,S-EDDS formed (mM) | | |
|---|---|---|---|
| Magnesium sulfate | TN-3 | TN-28 | TN-131 |
| not added | 11.8 | 11.6 | 11.9 |
| added | 19.7 | 19.3 | 19.3 |

REFERENTIAL EXAMPLE 1

Next, it was confirmed that the yields of S,S-EDDS achieved in Example 2 were those at the equilibration point.
(1) Cultivation:

The strain *Brevundimonas sp.* TN-3 was cultivated under the same conditions as those described in Example 2.
(2) Acquisition of Active Fraction Free from fumarase, etc.:

The procedure described in Example 2 was repeated.
(3) Reaction:

As the reaction mixture, use was made of one containing 34.2 mM of S,S-EDDS, 200 mM of a borate buffer, 17.1 mM of magnesium sulfate and the above-mentioned active fraction, having been adjusted to pH 8.0 with 6 N sodium hydroxide. For comparison, a mixture of the same composition but being free from magnesium sulfate was employed. These mixtures were each reacted at 30° C. for 4 to 10 days until S,S-EDDS was scarcely decomposed any more. During this process, the pH value of each reaction mixture was maintained at 8 with 6 N sulfuric acid.

After the completion of the reaction, S,S-EDDS in the mixture was determined by the same method as the one employed in Example 1.
(4) Results:

TABLE 3

| Magnesium sulfate | S,S-EDDS concentration (mM) at equilibrium |
|---|---|
| not added | 12.0 |
| added | 19.8 |

EXAMPLE 3

(1) Cultivation:

The strain *Brevundimonas sp.* TN-3 was cultivated under the same conditions as those described in Example 2.

(2) Acquisition of Active Fraction Free from Fumarase, etc.:
   The procedure described in Example 2 was repeated.
(3) Reaction:
   As the reaction mixture, use was made of those containing 68.4 mM of fumaric acid, 34.2 mM of ethylenediamine, 200 mM of a borate buffer, magnesium sulfate at each concentration as specified in Table 4 and the above-mentioned active fraction, having been adjusted to pH 8.0 with 6 N sodium hydroxide. These mixtures were each reacted at 30° C. for 4 to 10 days until S,S-EDDS was scarcely formed any more. During this process, the pH value of each reaction mixture was maintained at 8 with 6 N sodium hydroxide.
   After the completion of the reaction, S,S-EDDS in the mixture was determined by the same method as the one employed in Example 1.
(4) Results:

TABLE 4

| Magnesium sulfate (mM) | S,S-EDDS formed (mM) |
| --- | --- |
| not added | 11.2 |
| 17.1 | 19.2 |
| 34.2 | 25.7 |
| 68.4 | 29.1 |

EXAMPLE 4

(1) Cultivation:
   The procedure described in Example 3 was repeated.
(2) Acquisition of Active Fraction Free from Fumarase, etc.:
   The procedure described in Example 2 was repeated.
(3) Reaction:
   As the reaction mixture, use was made of one containing 68.4 mM of fumaric acid, 34.2 mM of ethylenediamine, 200 mM of a borate buffer, 51.3 mM of magnesium sulfate and the above-mentioned active fraction, having been adjusted to pH 8.0 with 6 N sodium hydroxide. A mixture of the same composition but being free from magnesium sulfate was also employed. These mixtures were each reacted at 20, 30 and 40° C. for 4 to 10 days until S,S-EDDS was scarcely formed any more. During this process, the pH value of each reaction mixture was maintained at a constant level with 6 N sodium hydroxide.
   After the completion of the reaction, S,S-EDDS in the mixture was determined by the same method as the one employed in example 1.
(4) Results:

TABLE 5

| | S,S-EDDS formed (mM) | |
| --- | --- | --- |
| Temperature(° C.) | No addition | Magnesium sulfate added |
| 20 | 13.7 | 29.3 |
| 30 | 11.6 | 27.1 |
| 40 | 8.1 | 26.9 |

EXAMPLE 5

Cultivation:
   The procedure described in Example 3 was repeated.
Acquisition of Active Fraction Free from Fumarase, etc.:
   The procedure described in Example 2 was repeated.
Reaction:
   As the reaction mixture, use was made of those containing 68.4 mM of fumaric acid, 34.2 mM of ethylenediamine, 200 mM of a borate buffer, 51.3 mM of magnesium sulfate and the above-mentioned active fraction, having been adjusted to pH 6, 7, 8 and 9 with 6 N sodium hydroxide Mixtures of the same composition but being free from magnesium sulfate were also employed. These mixtures were each reacted at 30° C. for 4 to 10 days until S,S-EDDS was scarcely formed any more. During this process, the pH value of each reaction mixture was maintained at a constant level with 6 N sodium hydroxide.
   After the completion of the reaction, S,S-EDDS in the mixture was determined by the same method as the one employed in Example 1.
(4) Results:

TABLE 6

| | S,S-EDDS formed (mM) | |
| --- | --- | --- |
| pH | No addition | Magnesium sulfate added |
| 6 | 9.2 | 17.9 |
| 7 | 10.4 | 23.1 |
| 8 | 11.6 | 27.1 |
| 9 | 11.4 | 30.0 |

EXAMPLE 6

(1) Cultivation:
   The procedure described in Example 3 was repeated.
(2) Acquisition of Active Fraction Free from Fumarase, etc.:
   The procedure described in Example 2 was repeated.
(3) Reaction:
   As the reaction mixture, use was made of those containing fumaric acid, ethylenediamine and magnesium hydroxide each at the concentration as specified in Table 7 and the above-mentioned active fraction, having been adjusted to pH 8.5 with 6 N sodium hydroxide. These mixtures were each reacted at 30° C. for 10 to 30 days until S,S-EDDS was scarcely formed any more. During this process, the pH value of each reaction mixture was maintained at 8.5 with 12 N sodium hydroxide.
   After the completion of the reaction, S,S-EDDS in the mixture was determined by the same method as the one employed in example 1.
(4)Results:

TABLE 7

| Fumaric acid (mM) | Ethylenediamine (mM) | Magnesium hydroxide (mM) | S,S-EDDS formed (mM) |
| --- | --- | --- | --- |
| 342 | 171 | 0 | 102 |
| 342 | 171 | 257 | 155 |
| 684 | 342 | 0 | 238 |
| 684 | 342 | 513 | 319 |
| 1232 | 616 | 0 | 488 |
| 1232 | 616 | 924 | 580 |

EXAMPLE 7

Cultivation:
   The procedure described in Example 2 was repeated.
Acquisition of Active Fraction Free from Fumarase, etc.:
   The procedure described in Example 2 was repeated.
(3) Reaction:
   As the reaction mixture, use was made of those containing 68.4 mM of fumaric acid, 34.2 mM of ethylenediamine, 200 mM of a borate buffer, 17.1 mM (in terms of the concentration as metal) of each metal compound as specified in Table 8 and the above-mentioned active fraction, having been adjusted to pH 8 with 6 N sodium hydroxide. For comparison, a mixture of the same composition but being free from any metal compound was employed. These mixtures were each reacted at 30° C. for 10 days. The pH value of each reaction mixture was maintained at 8 with the use of 6 N sulfuric acid or 6 N sodium hydroxide, if needed.

After the completion of the reaction, S,S-EDDS in the mixture was determined by the same method as the one employed in Example 1.

(4) Results:

TABLE 8

| Metal compound | S,S-EDDS formed (mM) | | |
|---|---|---|---|
| | TN-3 | TN-28 | TN-131 |
| not added | 11.8 | 11.6 | 11.9 |
| ferrous sulfate | 19.4 | 19.5 | 19.5 |
| ferric sulfate | 19.8 | 19.4 | 19.9 |
| zinc chloride | 19.6 | 19.2 | 19.7 |
| copper sulfate | 20.1 | 19.7 | 20.3 |
| nickel chloride | 16.2 | 14.5 | 16.0 |
| aluminum sulfate | 20.3 | 20.1 | 20.3 |
| strontium chloride | 14.0 | 13.9 | 14.2 |
| barium chloride | 13.1 | 13.0 | 13.2 |
| titanium tetrachloride | 13.1 | 12.8 | 13.0 |

EXAMPLE 8

(1) Cultivation:
The procedure described in Example 2 was repeated.
(2) Acquisition of Active Fraction Free from Fumarase, etc.:
The procedure described in Example 2 was repeated.
(3) Reaction:
The procedure described in Example 7 was repeated but using calcium chloride and manganese sulfate as the metal compounds.
(4) Results:

TABLE 9

| Metal compound | S,S-EDDS formed (mM) | | |
|---|---|---|---|
| | TN-3 | TN-28 | TN-131 |
| not added | 11.8 | 11.6 | 11.9 |
| calcium chloride | 16.3 | 15.6 | 16.0 |
| manganese sulfate | 25.2 | 24.6 | 24.5 |

REFERENTIAL EXAMPLE 2

Next, it was confirmed that the yields of S,S-EDDS achieved in Examples 7 and 8 were those at the equilibration point.
(1) Cultivation:
The strain Brevundimonas sp. TN-3 was cultivated under the same conditions as those described in Example 2.
(2) Acquisition of Active Fraction Free from Fumarase, etc.:
The procedure described in Example 2 was repeated.
(3) Reaction:
As the reaction mixture, use was made of those containing 34.2 mM of S,S-EDDS, 200 mM of a borate buffer, 17.1 mM of each metal compound and the above-mentioned active fraction, having been adjusted to pH 8.0 with 6 N sodium hydroxide. For comparison, a mixture of the same composition but being free from any metal compound was employed. These mixtures were each reacted at 30° C. for 4 to 10 days until S,S-EDDS was scarcely decomposed any more. During this process, the pH value of each reaction mixture was maintained at 8 with 6 N sodium hydroxide or 6 N sulfuric acid.

After the completion of the reaction, S,S-EDDS in the mixture was determined by the same method as the one employed in Example 1.

(4) Results:

TABLE 10

| Metal compound | S,S-EDDS concentration (mM) at equilibrium |
|---|---|
| not added | 12.0 |
| ferrous sulfate | 19.2 |
| ferric sulfate | 19.6 |
| zinc chloride | 19.6 |
| copper sulfate | 19.7 |
| nickel chloride | 16.5 |
| aluminum sulfate | 20.0 |
| strontium chloride | 14.5 |
| barium chloride | 13.3 |
| titanium tetrachloride | 13.0 |
| calcium chloride | 16.5 |
| manganese sulfate | 24.6 |

EXAMPLE 9

(1) Cultivation:
The procedure described in Example 3 was repeated.
(2) Acquisition of Active Fraction Free from Fumarase, etc.:
The procedure described in Example 2 was repeated.
(3) Reaction:
As the reaction mixture, use was made of those containing 68.4 mM of fumaric acid, 34.2 mM of ethylenediamine, 200 mM of a borate buffer, ferric sulfate at each concentration as specified in Table 11 and the above-mentioned active fraction, having been adjusted to pH 8 with 6 N sodium hydroxide. These mixtures were each reacted at 30° C. for 4 to 10 days until S,S-EDDS was scarcely formed any more. During the process, the pH value of each reaction mixture was maintained at 8 with 6 N sulfuric acid.

After the completion of the reaction, S,S-EDDS in the mixture was determined by the same method as the one employed in Example 1.

(4) Results:

TABLE 11

| Ferric sulfate (mM) | S,S-EDDS formed (mM) |
|---|---|
| not added | 11.2 |
| 8.55 (17.1 as iron) | 19.5 |
| 17.1 (34.2 as iron) | 27.4 |

EXAMPLE 10

(1) Cultivation:
The procedure described in Example 3 was repeated.
Acquisition of Active Fraction Free from Fumarase, etc.:
The procedure described in Example 2 was repeated.
Reaction:
As the reaction mixture, use was made of one containing 68.4 mM of fumaric acid, 34.2 mM of ethylenediamine, 200 mM of a borate buffer, 17.1 mM (34.2 mM as iron) of ferric sulfate and the above-mentioned active fraction, having been adjusted to pH 8 with 6 N sodium hydroxide. A mixture of the same composition but being free from ferric sulfate was also employed for comparison. These mixtures were reacted at 20, 30 and 40° C. for 4 to 10 days until S,S-EDDS was scarcely formed any more. During the process, the pH value of each reaction mixture was maintained at 8 with 6 N sulfuric acid.

After the completion of the reaction, S,S-EDDS in the mixture was determined by the same method as the one employed in example1.

(4) Results:

TABLE 12

| Temperature (° C.) | S,S-EDDS formed (mM) | |
| --- | --- | --- |
| | Not added | Ferric sulfate added |
| 20 | 13.7 | 27.3 |
| 30 | 11.6 | 26.2 |
| 40 | 8.1 | 23.7 |

EXAMPLE 11

(1) Cultivation:

The procedure described in Example 3 was repeated.

(2) Acquisition of Active Fraction Free from Fumarase, etc.:

The procedure described in Example 2 was repeated.

(3) Reaction:

As the reaction mixture, use was made of those containing 68.4 mM of fumaric acid, 34.2 mM of ethylenediamine, 200 mM of a borate buffer, 17.1 mM (34.2 mM as iron) of ferric sulfate and the above-mentioned active fraction, having been adjusted to pH 6, 7, 8 and 9 with 6 N sodium hydroxide. Mixtures of the same composition but being free from ferric sulfate were also employed for comparison. These mixtures were reacted at 30° C. for 4 to 10 days until S,S-EDDS was scarcely formed any more. During the process, the pH value of each reaction mixture was maintained at a constant level with 6 N sulfuric acid.

After the completion of the reaction, S,S-EDDS in the mixture was determined by the same method as the one employed in Example 1.

(4) Results:

TABLE 13

| pH | S,S-EDDS formed (mM) | |
| --- | --- | --- |
| | Not added | Ferric sulfate added |
| 6 | 9.2 | 30.0 |
| 7 | 10.4 | 27.82 |
| 8 | 11.6 | 26.2 |
| 9 | 11.4 | 23.9 |

EXAMPLE 12

Cultivation:

The procedure described in Example 3 was repeated.

(2) Aquisition of Active Fraction Free from Fumarase, etc.:

The procedure described in Example 2 was repeated.

(3) Reaction:

As the reaction mixture, use was made of those containing 342 mM of fumaric acid, 171 mM of ethylenediamine, 171 mM of calcium hydroxide or ferric hydroxide as a metal compound and the above-mentioned active fraction, having been adjusted to each pH value as specified in Table 14 with 6 N sodium hydroxide. A mixture of the same composition but containing neither calcium compound nor iron compound was also emmployed for comparison. These mixtures were reacted at 30° C. for 10 to 20 days until S,S-EDDS was scarcely formed any more. During the process, the pH value of each reaction mixture was maintained at a constant level with 6 N sodium hydroxide or 6 N sulfuric acid.

After the completion of the reaction, S,S-EDDS in the mixture was determined by the same method as the one employed in Example 1.

(4) Results:

TABLE 14

| Metal compound | pH | S,S-EDDS formed (mM) |
| --- | --- | --- |
| not added | 8.5 | 102 |
| calcium hydroxide | 8.5 | 132 |
| ferric hydroxide | 7 | 149 |

EXAMPLE 13

(1) Cultivation:

The procedure described in Example 1 was repeated.

(2) Acquisition of Cells:

The procedure described in Example 1 was repeated.

(2) Reaction:

As the reaction mixture, use was made of those containing 200 mM of fumaric acid, 200 mM of ethylenediamine, 100 mM of ferrous hydroxide or ferric hydroxide and the above-mentioned cells, having been adjusted to pH 8.0 with 6 N sodium hydroxide. For comparison, a mixture of the same composition but being free from iron was employed. These mixtures were each reacted at 30° C. for 24 hours under shaking.

S,S-EDDS in the mixture was determined by the same method as the one employed in Example 1.

(4) Results:

TABLE 15

| Strain | Iron compound (100 mM as iron) | S,S-EDDS formed (mM) |
| --- | --- | --- |
| TN-3 | none | 12.0 |
| | ferrous hydroxide | 22.1 |
| | ferric hydroxide | 24.2 |
| ATCC 9760 | none | 0.3 |
| | ferric hydroxide | 0.5 |
| KK-5 | none | 14.5 |
| | ferric hydroxide | 25.0 |
| KK-9 | none | 8.0 |
| | ferric hydroxide | 15.4 |
| TN-51 | none | 15.9 |
| | ferric hydroxide | 20.5 |
| TN-131 | none | 10.7 |
| | ferric hydroxide | 20.8 |
| KK-3 | none | 0.1 |
| | ferric hydroxide | 0.3 |
| KK-6 | none | 15.2 |
| | ferric hydroxide | 26.7 |
| TN-28 | none | 20.0 |
| | ferric hydroxide | 25.8 |
| TN-30 | none | 17.0 |
| | ferric hydroxide | 30.9 |

EXAMPLE 14

(1) Cultivation:

The strains Brevundimona sp. TN-3 and *Acidovorax sp.* TN-51 were cultivated under the same conditions as those described in Example 1.

(2) Acquisition of Cell:

The procedure described in Example 1 was repeated.

(3) Reaction:

The reaction mixture containing 200 mM of fumaric acid, 200 mM of 1,3-propanediamine, 1,2-propanediamine, 1,3-cyclohexylenediamine or 1,3-phenylenediamine, 100 mM of magnesium sulfate and the above-mentioned cells, having been adjusted to pH 8.0 with 6 N sodium hydroxide, were prepared. For comparison, a mixture of the same composition but being free from magnesium sulfate was employed. These mixtures were each reacted at 30° C. under shaking for 24 hours.

The products were quantified and the stereochemical characters were analyzed by the methods as the one employed in Example 1.

(4) Results:

TABLE 16

| Products | Magnesium sulfate | Products formed (mM) | |
|---|---|---|---|
| | | TN-3 | TN-51 |
| S,S-1,3-Propanediamine-N,N'-disuccinic acid | not added | 18 | 20 |
| | added | 37 | 51 |
| S,S-1,2-Propanediamine-N,N'-disuccinic acid | not added | 17 | 21 |
| | added | 40 | 57 |
| S,S-1,3-Cyclohexylenediamine-N,N'-disuccinic acid | not added | 13 | 11 |
| | added | 26 | 35 |
| S,S-1,3-Phenylenediamine-N,N'-disuccinic acid | not added | 15 | 17 |
| | added | 26 | 28 |

While the invention has been described in detail and with reference to specific embodiments thereof, it will be apparent to one skilled in the art that various changes and modifications can be made therein without departing from the spirit and scope thereof.

What is claimed is:

1. A process for producing an optically active aminopolycarboxylic acid represented by the following general formula (II) comprising reacting a mixture of a diamine represented by the following general formula (I) with fumaric acid using a microorganism having a lyase activity or an extract thereof, wherein said reacting is carried out in the presence of at least one metal ion selected from the group consisting of an alkaline earth metal, iron, zinc, copper, nickel, aluminum, titanium and manganese:

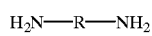 (I)

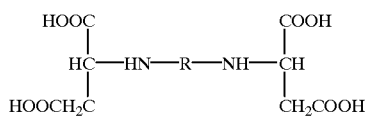 (II)

wherein R represents an alkylene, cyclohexylene or phenylene group.

2. The process of claim 1, wherein said metal ion is selected from the group consisting of Mg(II), Ca(II), Sr(II), Ba(II), Fe(II), Fe(III), Zn(II)., Cu(II), Ni(II), Al(III), Ti(IV) and Mn(II).

3. The process of claim 1, wherein said optically active aminopolycarboxylic acid represented by formula (II) is an S,S-aminopolycarboxylic acid.

4. The process of claim 3, wherein said S,S-aminopolycarboxylic acid is selected from the group consisting of S,S-ethylenediamine-N,N'-disuccinic acid, S,S-1,2-propanediamine-N,N'-disuccinic acid, S,S-1,3-propanediamine-N,N'-disuccinic acid, S,S-2-methyl-1,3-propanediamine-N,N'-disuccinic acid, S,S-1,2-cyclohexylenediamine-N,N'-disuccinic acid, S,S-1,3-cyclohexylenediamine-N,N'-disuccinic acid, S,S-1,4-cyclohexylenediamine-N,N'-disuccinic acid, S,S-1,2-phenylenediamine-N,N'-disuccinic acid, S,S-1,3-phenylenediamine-N,N'-disuccinic acid, and S,S-1,4-phenylenediamine-N,N'-disuccinic acid.

5. The process of claim 4, wherein said S,S'-aminopolycarboxylic acid is S,S-ethylenediamine-N,N'-disuccinic acid.

6. The process of claim 1, wherein said reacting is carried out at a pH of from 4 to 11.

7. The process of claim 6, wherein said reacting is carried out at a pH of from, 6 to 10.

8. The process of claim 1, wherein the concentration of diamine is from 0.01M to 2M and the concentration of fumaric acid is from 0.01M to saturation.

9. The process of claim 1, wherein a metal compound as the source of said metal ion is present in an amount of from 0.01 to 2 times, by mol in terms of the metal, as much as the theoretical amount of the optically active aminopolycarboxylic acid product represented by formula (II).

* * * * *